United States Patent
Ishiyama

(10) Patent No.: US 10,247,660 B2
(45) Date of Patent: Apr. 2, 2019

(54) LASER DISPLACEMENT METER AND LASER ULTRASONIC INSPECTION APPARATUS USING THE SAME

(71) Applicant: HITACHI, LTD., Tokyo (JP)

(72) Inventor: Kazuo Ishiyama, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 16/005,058

(22) Filed: Jun. 11, 2018

(65) Prior Publication Data
US 2019/0033201 A1  Jan. 31, 2019

(30) Foreign Application Priority Data
Jul. 25, 2017  (JP) .................... 2017-143145

(51) Int. Cl.
| | | |
|---|---|---|
| *G01N 21/17* | (2006.01) | |
| *G01H 9/00* | (2006.01) | |
| *H01S 5/40* | (2006.01) | |
| *G01B 11/02* | (2006.01) | |
| *H01S 5/00* | (2006.01) | |

(52) U.S. Cl.
CPC ....... *G01N 21/1702* (2013.01); *G01B 11/026* (2013.01); *G01H 9/008* (2013.01); *H01S 5/0071* (2013.01); *H01S 5/0078* (2013.01); *H01S 5/4087* (2013.01); *G01N 2201/0697* (2013.01)

(58) Field of Classification Search
CPC ........... G01N 21/1702; G01N 29/2418; G01N 29/14; G01N 29/04; G01B 11/026; G01B 17/00; H01S 5/408; G01H 9/008
See application file for complete search history.

(56) References Cited

U.S. PATENT DOCUMENTS

| | | | | |
|---|---|---|---|---|
| 5,526,338 | A * | 6/1996 | Hasman | G11B 7/0037 369/102 |
| 2007/0157730 | A1* | 7/2007 | Ochiai | F22B 37/003 73/627 |
| 2011/0286005 | A1* | 11/2011 | Yamamoto | B23K 31/125 356/511 |
| 2015/0062555 | A1* | 3/2015 | Kim | G01S 17/87 356/4.01 |
| 2015/0260640 | A1 | 9/2015 | Sharples et al. | |
| 2016/0109290 | A1* | 4/2016 | Klennert | G01J 9/00 356/416 |

FOREIGN PATENT DOCUMENTS

JP  2015-505362 A  2/2015

\* cited by examiner

*Primary Examiner* — Maurice C Smith
(74) *Attorney, Agent, or Firm* — Volpe and Koenig, P.C.

(57) ABSTRACT

A laser displacement meter includes: a laser array beam source unit including a plurality of lasers emitting beams with different wavelengths; a lens array unit including a plurality of lenses for focusing laser beams; a reflected beam lens array unit including a plurality of focusing lenses for focusing the beam reflected on the surface of the object; an optical filter array unit including a plurality of optical filters through which the reflected beam is selectively transmitted; and a photodetector array unit including a plurality of photodetectors for detecting the beam transmitted through the optical filters.

8 Claims, 4 Drawing Sheets

LASER DISPLACEMENT METER AND LASER ULTRASONIC INSPECTION APPARATUS USING THE SAME

CROSS-REFERENCE TO RELATED APPLICATION

This application claims the priority of Japanese Patent Application No. 2017-143145 filed Jul. 25, 2017, which is incorporated herein by reference in its entirety.

TECHNICAL FIELD

The present invention relates to ultrasonic technology, and particularly to a laser displacement meter and a laser ultrasonic inspection apparatus.

BACKGROUND ART

The laser ultrasonic inspection apparatus includes an ultrasonic excitation unit with a laser and an ultrasonic detection unit with a laser. The ultrasonic excitation by the laser is performed by irradiating test pieces with a pulsed laser beam (excitation laser). When the power density of the laser beam is low, thermal stress is generated due to the rapid heating-cooling process on a micro region of the surface, and the generated thermal stress serves as the source of distortion of the material, whereby ultrasonic signals are generated (a thermoelastic mode).

On the other hand, when the power density of the laser beam is high, a surface layer of the test piece is turned into plasma, and the pressure is applied to the test piece as a reaction to the expansion of plasma, whereby ultrasound is generated (an ablation mode).

The reception of ultrasonic waves by a laser is performed by measurement of the surface displacement induced by ultrasonic waves with a laser displacement meter. As the laser displacement meter, there is a method of using deflection of beam by surface displacement which is called a knife edge method. The knife edge method is inexpensive, and a speckle knife edge detector (hereinafter, referred to as SKED) capable of being applied to a rough surface is disclosed in JP-T-2015-505362. Therefore, a practical and inexpensive laser ultrasonic inspection apparatus can be realized using a knife-edge type detector.

An example of related art includes JP-T-2015-505362.

SUMMARY OF THE INVENTION

Technical Problem

For the measurement using laser ultrasonic testing, scanning of excitation laser and scanning of detection laser are necessary.

In the knife-edge type laser displacement meter, since the detection laser beam is irradiated at an angle to the surface of the test piece and the probe beam (reflected beam on the surface of the test piece) is received by a detection unit, the irradiation beam and the probe beam are not coaxial. Therefore, since the detection unit is also necessary to be scanned when the detection laser beam is scanned, it is difficult to realize.

Therefore, it is preferable to increase the measurement time by fixing and arraying the position of the irradiation beam and the position of the detection beam in order to simultaneously measure at multiple points.

However, when the pitch of the array of photodetectors is small, or when the surface of the test piece is rough and thus the reflected beam is scattered, crosstalk occurs in which a signal leaks to adjacent photodetectors and noise increases, whereby the SN ratio may deteriorate.

An object of the invention is to provide a practical and inexpensive laser displacement meter capable of reducing noise and the measurement time.

Solution to Problem

A preferred embodiment of the invention provides a laser displacement meter for detecting reflected beam from an object to measure a displacement occurring in the object, the laser displacement meter including: a laser array beam source unit including a plurality of lasers beams with different wavelengths; a lens array unit including a plurality of lenses for focusing laser beams; a lens array unit including a plurality of focusing lenses for focusing the beam reflected on the object; an optical filter array unit including a plurality of optical filters through which the reflected beam is selectively transmitted; and a photodetector array unit including a plurality of photodetectors for detecting the beam transmitted through the optical filters.

Advantageous Effects of the Invention

According to the invention, it is possible to obtain a practical and inexpensive laser displacement meter capable of reducing noise and the measurement time.

DESCRIPTION OF THE EMBODIMENTS

Embodiment of the invention will be described in detail below with reference to the drawings.

[First Embodiment]

Figure 1:
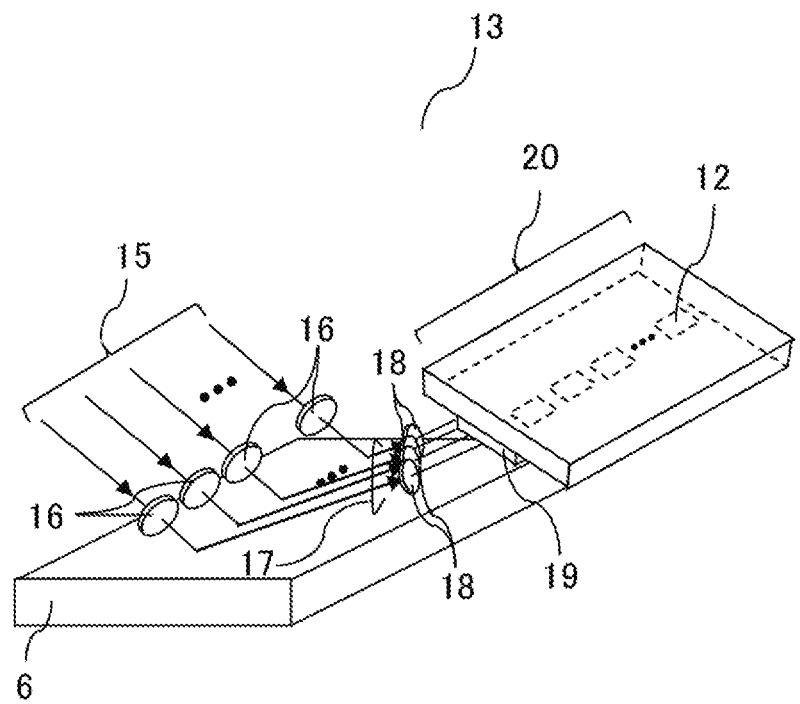
FIG. 1 is a perspective view illustrating a knife-edge type laser displacement meter using a multi-wavelength laser beam source according to an embodiment.
Figure 2:
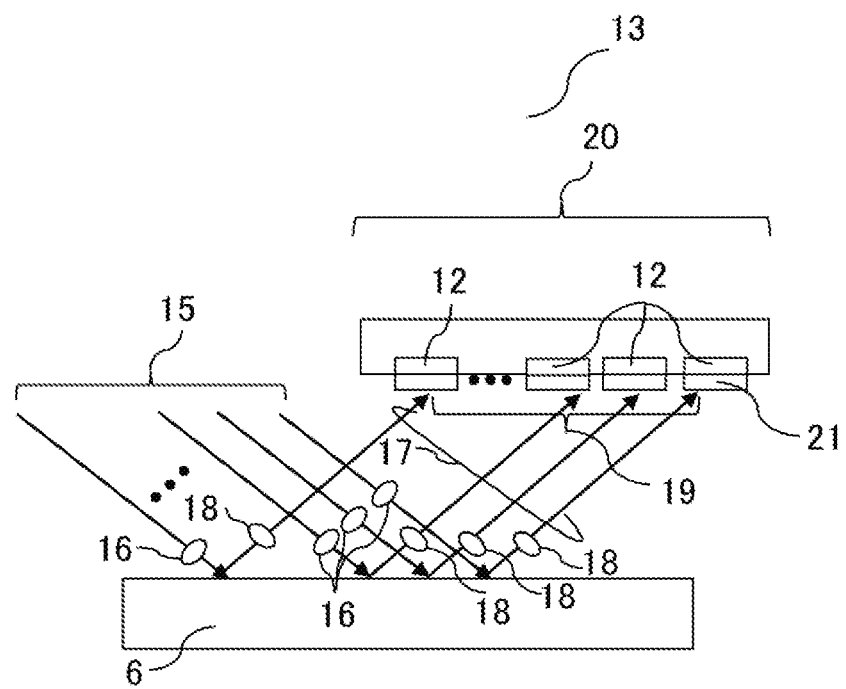
FIG. 2 is a side view illustrating of the knife-edge type laser displacement meter using the multi-wavelength laser beam source.

FIG. 1 is a perspective view of a laser displacement meter 13 of a first embodiment, and FIG. 2 is a side view of the laser displacement meter 13.

The laser displacement meter 13 includes a plurality of laser beams 15 having at least two different wavelengths, a focusing lens array 16 including a plurality of lenses for focusing the respective laser beams, a probe beam focusing lens 18 including a plurality of focusing lenses for focusing multi-wavelength probe beam 17 reflected on a surface of a test piece, an optical filter array 19 including a plurality of optical filters through which each focused probe beam is transmitted, and a photodetector array 20 including a plurality of knife-edge type photodetectors 12 that detects the beam transmitted through the optical filter.

Figure 7:
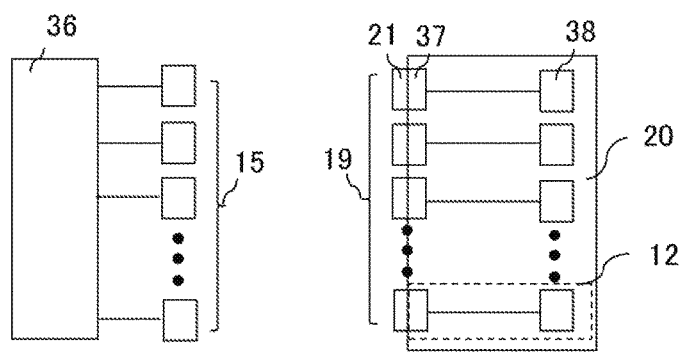
FIG. 7 is a view illustrating a configuration of a knife-edge type photodetector array, a multi-wavelength laser beam, and a power supply unit for a multi-wavelength laser.

Here, the knife-edge type photodetector array 20 includes a photodiode 37 and an electric signal amplifier 38 (see FIG. 7).

The multi-wavelength laser beam 15 is focused by the focusing lens array 16, and is irradiated on the surface of a test piece 6. The irradiated beam 15 is reflected on the surface of the test piece to become a probe beam 17, and the probe beam is focused by the focusing lens 18 and is incident on the optical filter array 19. Since the optical filter has a characteristic of transmitting only a beam of a specific wavelength range, the beam incident on each of the optical filters 21 is selectively transmitted, and is detected by each of the knife-edge type photodetectors 12 disposed behind the optical filters 21.

In the knife-edge type photodetector 12 constituting the photodetector array 20, deflection of the probe beam occurs due to the displacement of the surface of the test piece, and an electric signal is generated in proportion to the amount of deflection. By use of the optical filter array, a so-called detector-to-detector crosstalk, some of the beams incident on a certain photodetector is incident on another photodetector, is reduced, and thus a noise component due to the crosstalk can be suppressed.

The crosstalk will be described herein. The beams 15 of the respective wavelengths are reflected on respective measurement positions on the surface of the test piece 6, and are incident on the respective knife-edge type photodetectors 12 of the photodetector array 20. That is, the respective measurement positions are in one-to-one correspondence with the respective photodetectors 12, and a certain photodetector is used to acquire only data at the corresponding measurement position. However, when the surface is rough, since the beam 15 is scattered, the beam reflected at a certain position is also incident on the photodetector other than the corresponding photodetector, and this beam becomes a noise component.

As a multi-wavelength laser beam source that emits the multi-wavelength laser beam 15, a solid laser, a semiconductor laser, or the like can be applied. The solid laser can realize a multi-wavelength laser by performing wavelength conversion using a nonlinear crystal (BBO, LBO, KTP, LiNO$_3$, or the like) for laser wavelength conversion.

The semiconductor laser can be widely varied in wavelength from a visible range to a near infrared range by a change of a semiconductor material, and can easily realize a multi-wavelength laser. As an optical filter of the optical filter array 19, a bandpass type filter having a multilayer film structure is preferable, but a low-pass filter or a high-pass filter may be used. As the knife-edge type photodetector, a two-division photodiode, a position sensitive detector, and a speckle knife edge detector (SKED) disclosed in JP-T-2015-505362 are preferable.

[Second Embodiment]

Since detection sensitivity of the knife-edge type photodetector 12 has wavelength dependency, ways of correcting sensitivity of the respective photodetectors 12 are necessary. The ways of correcting the sensitivity include the following (1) to (3).

(1) A way of correcting the sensitivity by controlling a current supplied from a multi-wavelength laser power supply unit 36 illustrated in FIG. 7 and adjusting an output of the respective multi-wavelength laser beams.

(2) A way of correcting the sensitivity by adjusting transmittance of the respective optical filters 21.

(3) A way of correcting the sensitivity by adjusting an amplification degree of the electric signal amplifier 38 in the knife-edge type photodetector 12 illustrated in FIG. 7. By the correction of the sensitivity, it is possible to obtain a true signal intensity level from the respective detectors.

[Third Embodiment]

Figure 3:
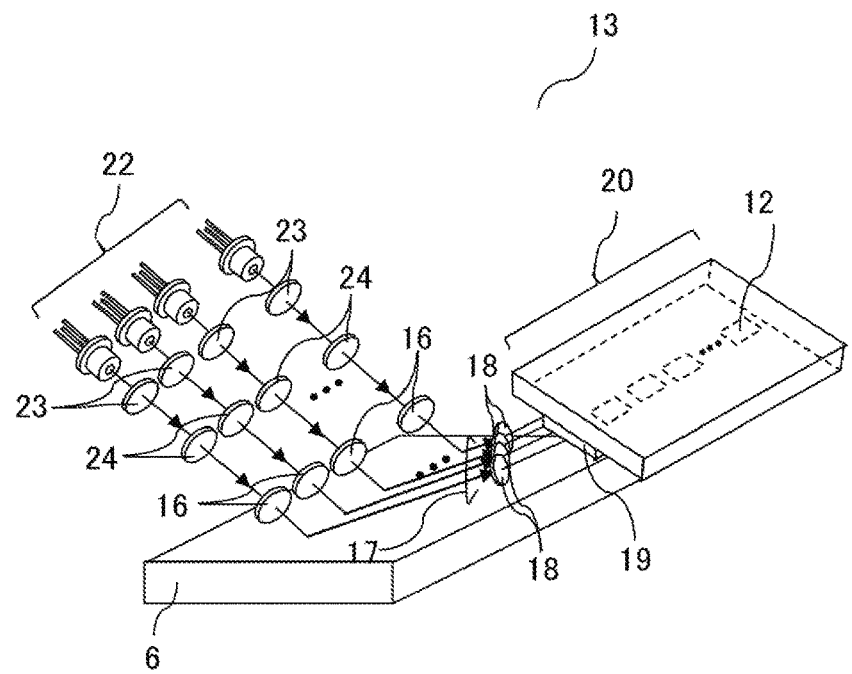
FIG. 3 is a view illustrating a knife-edge type laser displacement meter using a plurality of semiconductor laser beam source having different wavelengths.

FIG. 3 is a view illustrating a third embodiment in which a semiconductor laser is used as a multi-wavelength beam source of a laser displacement meter 13. The laser displacement meter 13 according to the third embodiment includes: a multi-wavelength laser beam source 22 including a plurality of semiconductor lasers having at least two different wavelengths; a lens array including a plurality of collimator lenses 23 for collimating the respective laser beams; a lens array including anamorphic lenses 24 for forming a collimated beam into a circular beam shape; a lens array including irradiation beam focusing lenses 16 for focusing the circular collimated beam on the surface of the test piece; a probe beam focusing lens 18 including a plurality of focusing lenses for focusing a multi-wavelength probe beam 17 obtained by reflected on the surface of the test piece; an optical filter array 19 including a plurality of optical filters through which the probe beam of a specific wavelength out of the respective focused probe beams is selectively transmitted; and a photodetector array 20 including a plurality of knife-edge type photodetectors 12 for detecting the beam transmitted through the optical filter.

Examples of materials of the semiconductor laser include a GaN-based material, an AlGaAs/GaAs-based material, and a GaInAsP/InP-based material. The semiconductor laser can be reduced in size. Compared to a solid laser, since the semiconductor laser has many types of wavelengths, it is possible to provide lasers with different kinds of wavelengths as laser beam sources.

[Fourth Embodiment]

Figure 4:
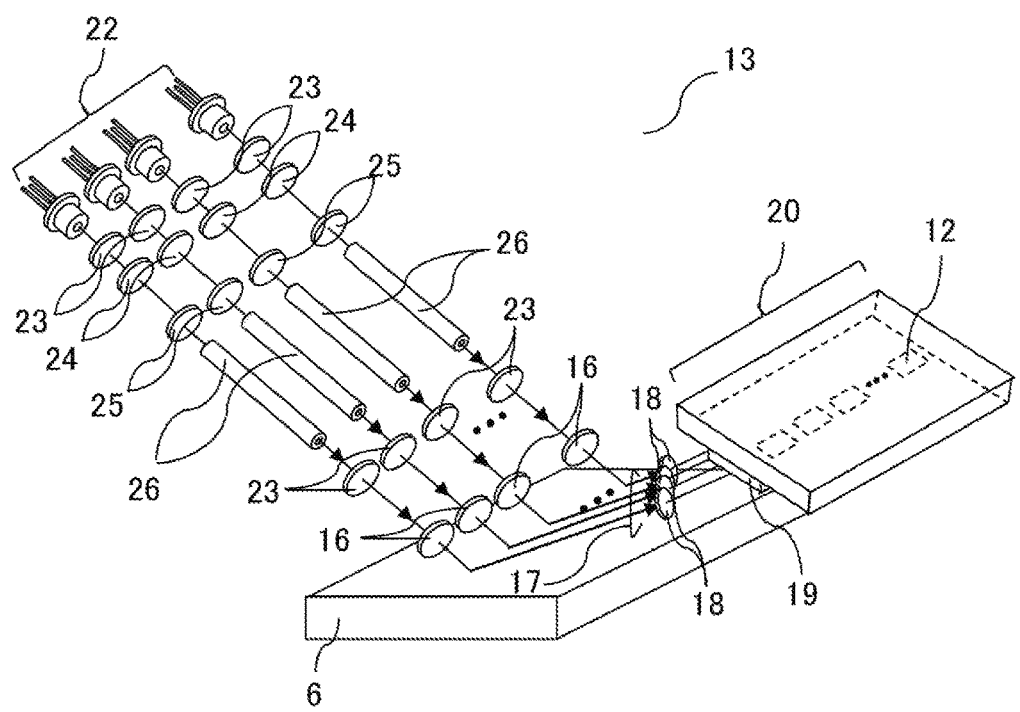
FIG. 4 is a view illustrating a knife-edge type laser displacement meter in which a plurality of semiconductor laser beam source having different wavelengths are coupled to a plurality of optical fibers.

FIG. 4 is a view illustrating a fourth embodiment in which an optical fiber is used in a laser displacement meter 13. The laser displacement meter 13 according to the fourth embodiment includes: a multi-wavelength laser beam source 22 including a plurality of semiconductor lasers having at least two different wavelengths; a lens array including a plurality of collimator lenses 23 for collimating the respective laser beams; a lens array including anamorphic lenses 24 for forming a collimated beam into a circular beam shape; a lens array including semiconductor laser focusing lenses 25 for focusing the collimated beam to allow it to be incident on an optical fiber 26; a lens array including collimator lenses 23 for collimating the beam emitted from the optical fiber 26; a lens array including irradiation beam focusing lenses 16 for focusing the circular collimated beam on the surface of the test piece; a probe beam focusing lens 18 including a plurality of focusing lenses for focusing a multi-wavelength probe beam 17 obtained by reflection of the laser beam, which is irradiated onto the test piece, on the surface of the test piece; an optical filter array 19 including a plurality of optical filters through which only the respective focused probe beams are selectively transmitted; and a photodetector array 20 including a plurality of knife-edge type photodetectors 12 for detecting the beam transmitted through the optical filter.

According to the fourth embodiment, since the optical fiber is used, the measurement of the test piece located away from the laser beam source is facilitated.

[Fifth Embodiment]

A fifth embodiment in which a guide beam is used in a laser displacement meter 13 will be described with reference to FIG. 1. At least two or more wavelengths of the multi-wavelength laser beam are set to a visible range. In a case where the beam having the wavelength within the visible range is used as the guide beam, it is easy to find out where the beam of each wavelength is incident on the surface of the test piece 6. For this reason, the user of the laser displacement meter 13 for measuring the displacement easily aligns the positions of the laser beams 15.

[Sixth Embodiment]

Figure 5:
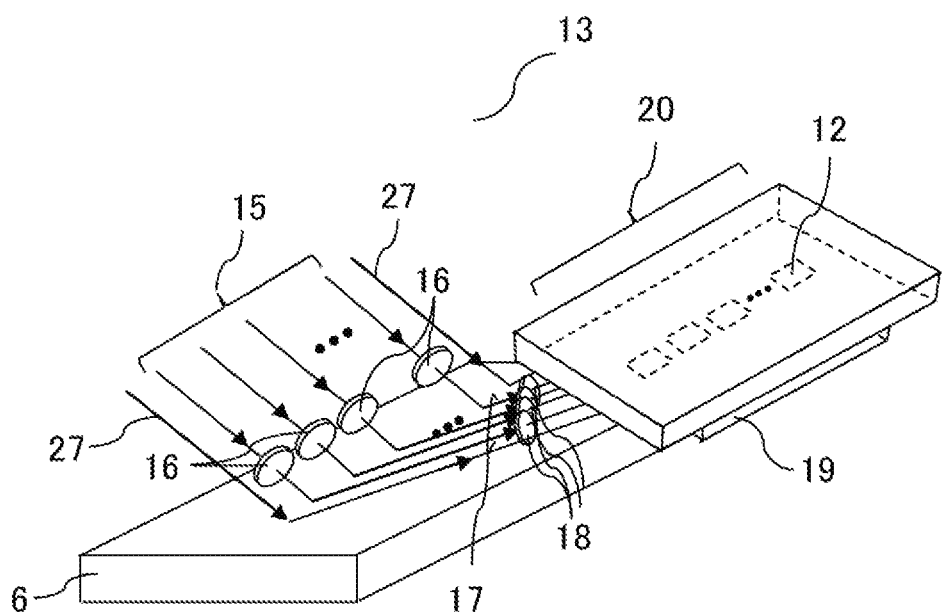
FIG. 5 is a view illustrating a knife-edge type laser displacement meter having a guide beam.

A sixth embodiment in which a guide beam is used in a laser displacement meter 13 will be described with reference to FIG. 5. The laser displacement meter 13 according to the sixth embodiment includes: a plurality of laser beams 15 having at least two different wavelengths; guide beams 27 that are located at both ends of the plurality of laser beams 15 and have wavelengths in the visible range; a lens array 16 including a plurality of lenses for focusing the plurality of laser beams 15; a probe beam focusing lens 18 including a plurality of focusing lenses for focusing a multi-wavelength probe beam 17 obtained by reflection on the surface of the test piece; an optical filter array 19 including a plurality of optical filters through which the probe beam of a specific wavelength out of the respective focused probe beams is selectively transmitted; and a photodetector array 20 including a plurality of knife-edge type photodetectors 12 for detecting the beam transmitted through the optical filter.

When the high-sensitivity wavelength range of the photodiode used for the knife-edge type photodetector 12 is out of the visible range, the wavelength of the laser beam 15 is preferably out of the visible range, and it is difficult to align the position of the laser beams 15. In this case, the guide beams 27 having the wavelength in the visible range are added to both ends of the plurality of laser beams 15, and thus the user of the laser displacement meter 13 easily align the positions of the laser beams 15.

[Seventh Embodiment]

Figure 6:
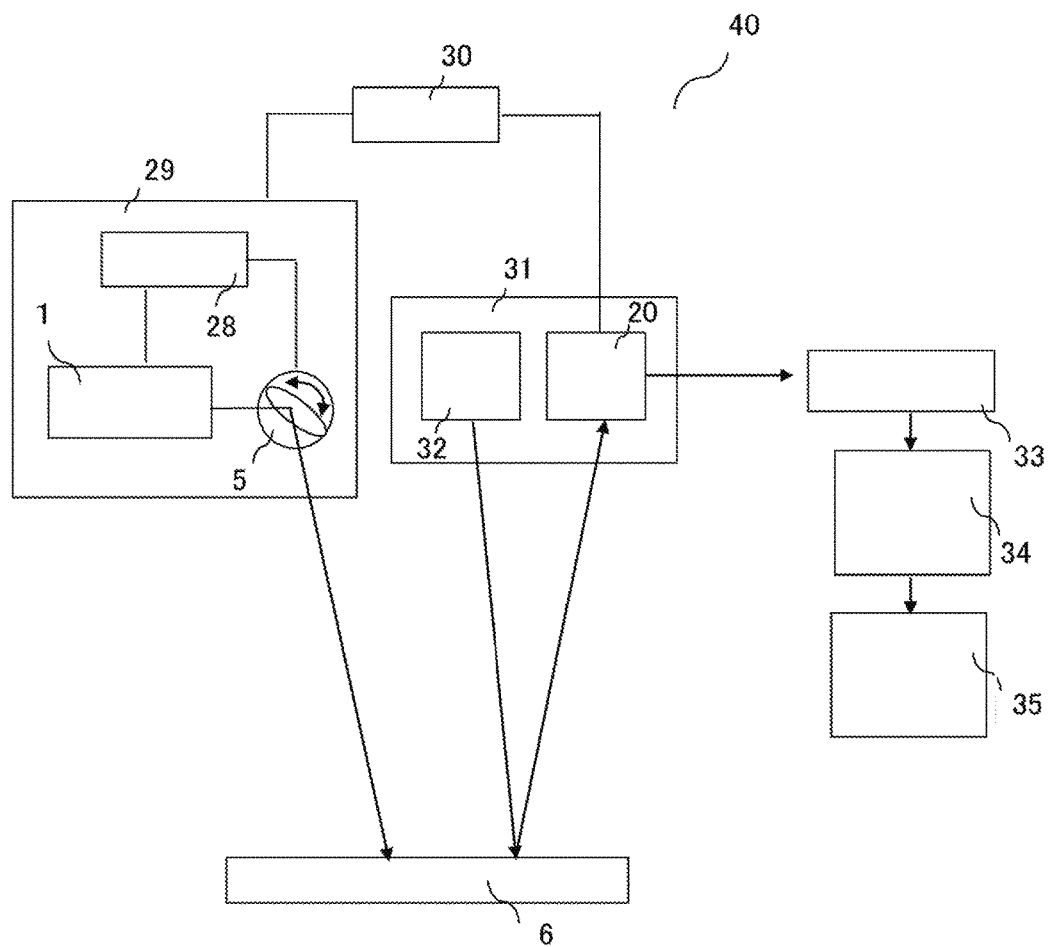
FIG. 6 is a block diagram of a laser ultrasonic inspection apparatus using a knife-edge type laser displacement meter array.

FIG. 6 is a block diagram of a laser ultrasonic inspection apparatus 40 according to a seventh embodiment in which a laser displacement meter 13 is used. The laser ultrasonic inspection apparatus 40 includes an ultrasonic generation unit 29, a detection unit 31, an inter-unit synchronization control unit 30, an A/D converter 33, a signal processing unit 34, and an imaging device 35. The ultrasonic generation unit 29 includes an excitation laser 1, a scanning mirror 5 for scanning the excitation laser 1, and a control unit 28 necessary for synchronizing the excitation laser and a scanning mirror, the control unit 28 being provided in the ultrasonic generation unit.

The detection unit 31 is the laser displacement meter 13 according to the first to sixth embodiments which includes the multi-wavelength laser beam source 32 and the knife-edge type photodetector array 20.

The synchronization control unit 30 synchronizes the ultrasonic generation unit 29 and the reception unit 31. The synchronization control unit 30 is necessary to synchronize the ultrasonic generation time by the ultrasonic generation unit 29 and the signal acquisition start time by the detection unit 31.

An output from the detection unit 31 is converted from an analog signal into a digital signal by the A/D converter 33, the signal processing unit 34 processes the digital signal converted by the A/D converter 33, and then a detection image is prepared by the imaging device 35. Here, the ultrasonic generation unit 29 may be a piezoelectric type or an electrostatic capacitance type ultrasonic generation element in addition to a pulsed laser.

What is claimed is:

1. A laser ultrasonic inspection apparatus comprising:
   a laser displacement meter, wherein the laser displacement meter includes:
      a laser array that includes a plurality of lasers emitting beams with different wavelengths,
      a lens array that includes a plurality of lenses for focusing the beams with different wavelengths on an object as focused beam,
      a reflected beam lens array that includes a plurality of focusing lenses for focusing a beam reflected by the object in response to the focused beam,
      an optical filter array that includes a plurality of optical filters through which the reflected beam is selectively transmitted to generate a filtered beam, and
      a photodetector array that includes a plurality of photodetectors for detecting the filtered beam;
   an ultrasonic sensor that generates ultrasonic waves; and
   a controller that synchronizes the ultrasonic sensor and the laser displacement meter.

2. The apparatus according to claim 1, wherein a sensitivity of the photodetector is adjusted based on the wavelengths of the plurality lasers.

3. The apparatus according to claim 1, wherein the laser array is formed from semiconductor lasers.

4. The apparatus according to claim 3, further comprising:
   an optical transmission medium that guides beam emitted from the semiconductor lasers.

5. The apparatus according to claim 3, wherein
   the laser array is configured such that multi-wavelength laser beams are set to a visible range so as to be used as a guide beam.

6. The apparatus according to claim 3, wherein
   in the laser displacement meter, wavelengths of two laser beams arranged at both ends of the laser array is within a visible range so as to be used as a guide beam.

7. The apparatus according to claim 1 further comprising:
   an imager that prepares an image based on a signal from the laser displacement meter.

8. The apparatus according to claim 1, wherein the photodetector is a knife-edge type photodetector.

* * * * *